US008986382B2

(12) United States Patent
Bentley et al.

(10) Patent No.: US 8,986,382 B2
(45) Date of Patent: Mar. 24, 2015

(54) TISSUE FIXATION AND REPAIR SYSTEMS AND METHODS

(75) Inventors: Ishmael Bentley, Eagan, MN (US); Dale Brady, New Brighton, MN (US); Emily Daley, Coon Rapids, MN (US); Mike E. Lancial, St. Louis Park, MN (US); Lawrence W. Wales, Maplewood, MN (US); Steven L. Griffith, Eden Prairie, MN (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 633 days.

(21) Appl. No.: 13/100,085

(22) Filed: May 3, 2011

(65) Prior Publication Data

US 2012/0283835 A1 Nov. 8, 2012

(51) Int. Cl.
*A61F 2/44* (2006.01)
*A61N 1/00* (2006.01)
*A61N 1/05* (2006.01)

(52) U.S. Cl.
CPC ................................. *A61N 1/0558* (2013.01)
USPC ...................................... 623/17.11; 607/117

(58) Field of Classification Search
USPC .......................................................... 607/117
See application file for complete search history.

(56) References Cited

U.S. PATENT DOCUMENTS

| 5,895,360 A * | 4/1999 | Christopherson et al. ..... 600/529 |
| 2003/0074023 A1 | 4/2003 | Kaplan et al. |
| 2005/0033393 A1 * | 2/2005 | Daglow ........................ 607/116 |
| 2006/0205995 A1 | 9/2006 | Browning |
| 2009/0210043 A1 * | 8/2009 | Reddy ........................... 607/127 |
| 2009/0259260 A1 * | 10/2009 | Bentley et al. ................ 606/300 |
| 2011/0264180 A1 * | 10/2011 | Hamilton ..................... 607/117 |

* cited by examiner

*Primary Examiner* — Jerry Cumberledge
*Assistant Examiner* — Nicholas Plionis
(74) *Attorney, Agent, or Firm* — Lowe Graham Jones PLLC; Bruce E. Black

(57) ABSTRACT

A system and method for securing an implantable medical device to an anatomical feature, such as bony structures and/or soft tissues near the spine. The system includes a tissue fixation device and a tissue fixation device delivery tool. The tissue fixation device includes at least one bone or tissue anchor and a connecting element coupled thereto. The tissue fixation device optionally includes a flexible anchoring strap for engaging the implantable medical device. The bone or tissue anchor are configured to be deployed into the anatomical feature, and the connecting element is tightened to secure the implantable medical device to the anatomical feature.

22 Claims, 13 Drawing Sheets

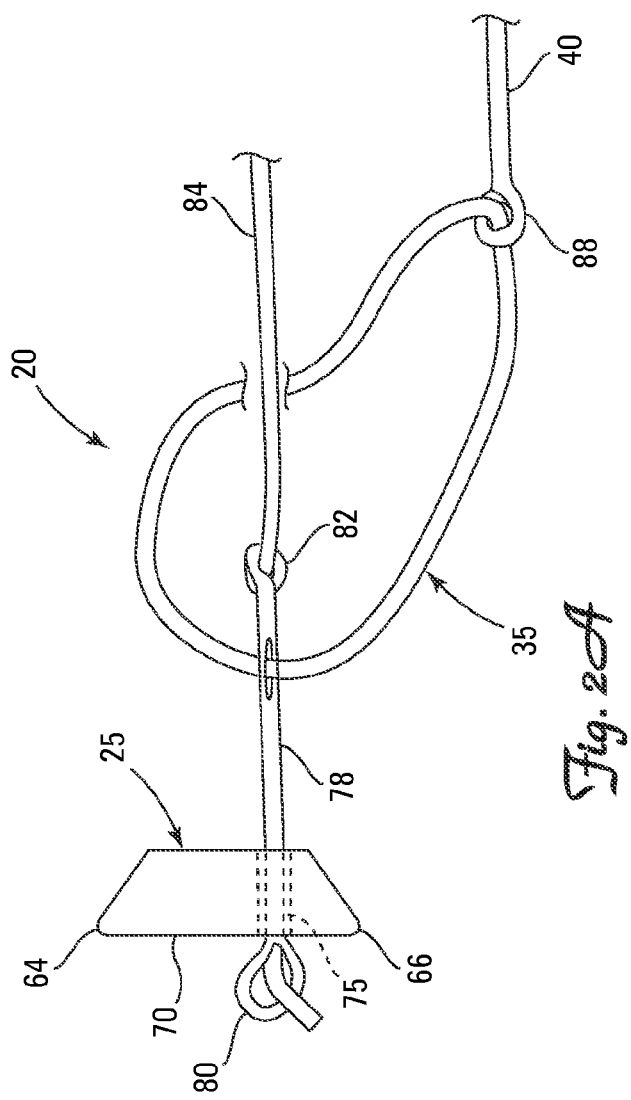
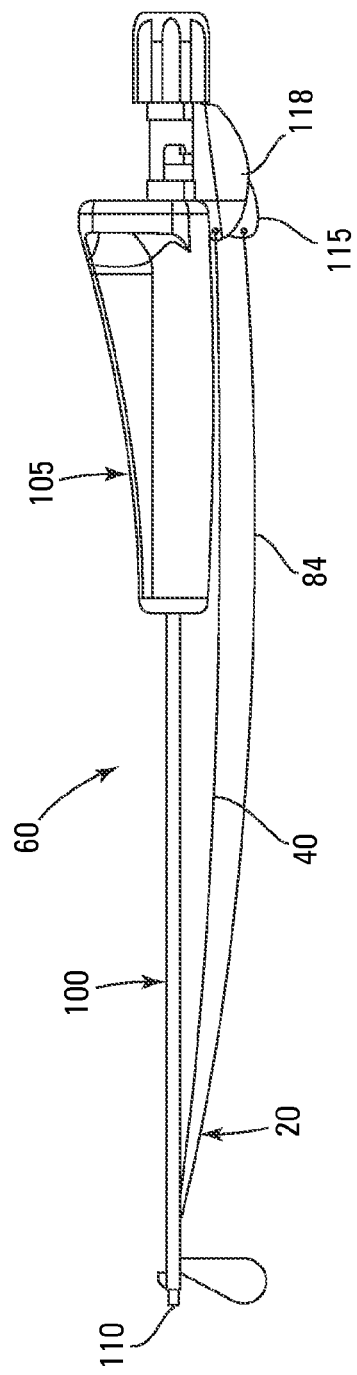
Fig. 2A
Fig. 2B

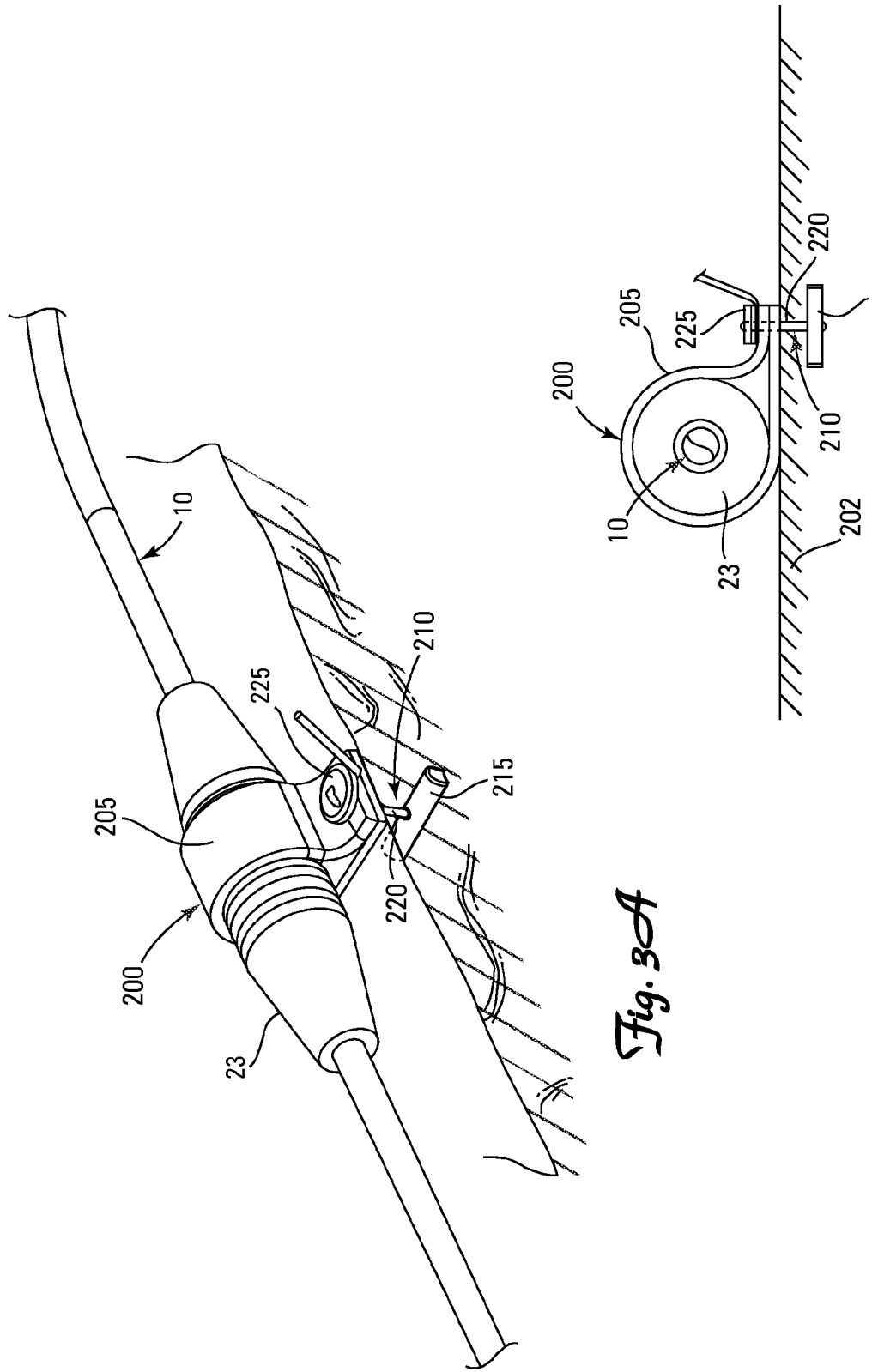

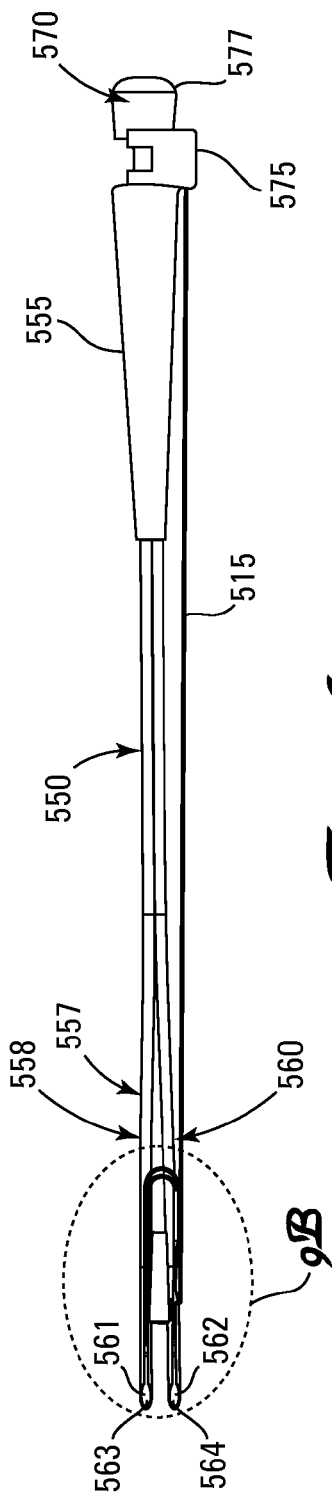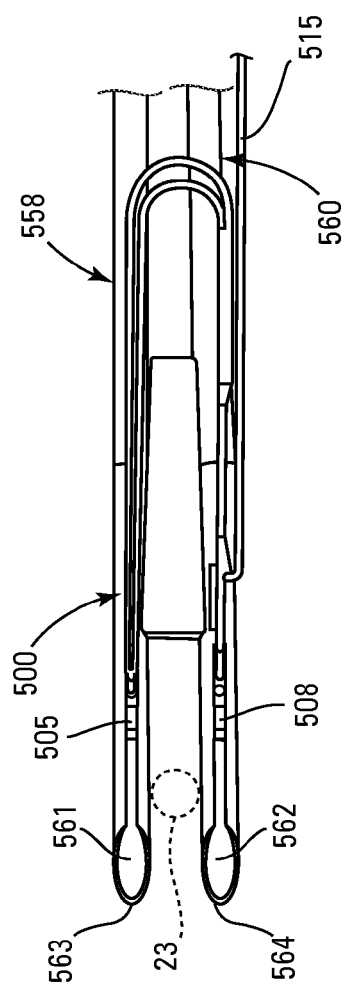

TISSUE FIXATION AND REPAIR SYSTEMS AND METHODS

TECHNICAL FIELD

The present invention relates to medical devices and methods for implanting implantable medical devices. More specifically, the invention relates to devices and methods for securing implantable medical devices to bony structures and soft tissues of a patient.

BACKGROUND

The implantation of various implantable medical devices requires securing the device to the patient's anatomy to prevent, or at least inhibit, unintended movement and/or migration of the implanted device. Exemplary such implantable medical devices include spinal stimulation leads, which are typically implanted adjacent to the patient's vertebral column and coupled to an implantable stimulator to provide selective nerve stimulation for pain management and the like. Such leads typically include a flexible insulative body and a compressible anchoring sleeve disposed about the lead body. In a conventional implantation procedure, sutures or other ligatures manually tied around the anchoring sleeve to secure the anchoring sleeve, and consequently the lead disposed therein, to soft tissues proximate the patient's spinal column. In these applications, the anchoring sleeve operates to delimit compressive forces on the lead itself imposed by the fixation sutures/ligatures.

SUMMARY

The present invention, in Example 1, is a method of securing an implantable medical device to or adjacent to an anatomical feature in a patient. The method comprises providing a fixation device coupled to a delivery tool, the delivery tool including a needle cannula having a distal tip, the fixation device including at least one anchor member and a flexible suture assembly including an adjustable suture loop coupled to the anchor member. The distal tip of the needle cannula is inserted into the anatomical feature. The at least one anchor member is ejected from the distal tip of the needle cannula into the anatomical feature. The implantable medical device is inserted within the adjustable suture loop, and a dimension of the adjustable suture loop is reduced to tighten the adjustable suture loop about the implantable medical device.

In Example 2, the method of Example 1 wherein the implantable medical device includes a flexible member and a compressible anchoring sleeve disposed about the flexible member, inserting the implantable medical device within the adjustable suture loop includes positioning the anchoring sleeve within the adjustable suture loop, and reducing the dimension of the adjustable suture loop to tighten the adjustable suture loop about the implantable medical device includes tightening the adjustable suture loop about the anchoring sleeve.

In Example 3, the method of either of Examples 1 or 2 wherein the at least one anchor member includes a bone anchor and the anatomical feature includes a bony structure.

In Example 4, the method of Example 3 wherein the bony structure is a vertebral body, and wherein the implantable medical device is a neurostimulation lead.

In Example 5, the method of either of Examples 3 or 4 wherein the fixation device further includes a soft tissue anchor slidably coupled to the adjustable suture loop, and wherein the anatomical feature further includes soft tissue proximate the vertebral body, and wherein the method further comprises removing the distal tip of the needle cannula from the vertebral body and subsequently inserting the distal tip of the needle cannula into the soft tissue and ejecting the soft tissue anchor into the soft tissue prior to reducing the dimension of the adjustable suture loop to tighten the adjustable suture loop about the anchoring sleeve.

In Example 6, the present invention is a method of securing an implantable medical device to or adjacent to an anatomical feature in a patient. The method comprises positioning the implantable medical device in proximity to the anatomical feature. A flexible anchoring strap is positioned against the implantable medical device such that the implantable medical device lies between the anatomical feature and at least a portion of the anchoring strap. The anchoring strap is secured to the anatomical feature using an anchoring element.

In Example 7, the method of Example 6 wherein positioning the flexible anchoring strap includes wrapping the anchoring strap about the implantable medical device and causing opposite ends of the anchoring strap to overlap.

In Example 8, the method of either of Examples 6 or 7 wherein securing the anchoring strap includes inserting a portion of the anchoring element through the overlapped ends of the anchoring strap and into the anatomical feature.

In Example 9, the method of any of Examples 6-8 wherein the anchoring element includes a tissue anchor, a flexible connecting element connected to the tissue anchor, and a locking element disposed on the connecting element, and wherein inserting the portion of the anchoring element through the overlapped ends of the anchoring strap includes inserting a distal end of a delivery tool through the overlapped ends of the anchoring strap and into the anatomical feature, ejecting the tissue anchor from the delivery tool and into the anatomical feature, withdrawing the distal end of the delivery tool from the anatomical feature and the overlapped ends of the anchoring strap, and deploying the locking element against a side of the anchoring strap opposite the anatomical feature so as to tighten the connecting element and secure the anchoring strap to the anatomical feature.

In Example 10, the method of Example 6 wherein positioning the anchoring strap against the implantable medical device includes positioning a first end of the anchoring strap against the anatomical feature at a first location and positioning a second end of the anchoring strap against the anatomical feature at a second location, the implantable medical device being positioned between the first and second locations such that the anchoring strap spans across and over the implantable medical device.

In Example 11, the method of Example 10 wherein securing the anchoring strap to the anatomical feature includes securing the first end of the anchoring strap to the anatomical feature using a first anchoring element, and securing the second end of the anchoring strap to the anatomical feature using a second anchoring element.

In Example 12, the method of either of Examples 10 or 11 wherein securing the first end of the anchoring strap to the anatomical feature includes inserting a portion of the first anchoring element through the first end of the anchoring strap and into the anatomical feature, and securing the second end of the anchoring strap to the anatomical feature includes inserting a portion of the second anchoring element through the second end of the anchoring strap and into the anatomical feature.

In Example 13, the method of any of Examples 10-12 wherein the first and second anchoring elements each include a tissue anchor, a flexible connecting element connected to the tissue anchor, and a locking element disposed on the connecting element, and wherein inserting the portion of the first anchoring element through the first end of the anchoring strap includes inserting a distal end of a first delivery tool through the first end of the anchoring strap and into the anatomical feature, ejecting the tissue anchor of the first anchoring element from the first delivery tool and into the anatomical feature, withdrawing the distal end of the first delivery tool from the anatomical feature and the first end of the anchoring strap, and deploying the locking element of the first anchoring element against a side of the first end of the anchoring strap opposite the anatomical feature so as to tighten the connecting element of the first anchoring element and secure the first end of the anchoring strap to the anatomical feature. Additionally, inserting the portion of the second anchoring element through the second end of the anchoring strap includes inserting a distal end of a second delivery tool through the second end of the anchoring strap and into the anatomical feature, ejecting the tissue anchor of the second anchoring element from the second delivery tool and into the anatomical feature, withdrawing the distal end of the second delivery tool from the anatomical feature and the second end of the anchoring strap, and deploying the locking element of the second anchoring element against a side of the second end of the anchoring strap opposite the anatomical feature so as to tighten the connecting element of the second anchoring element and secure the second end of the anchoring strap to the anatomical feature.

In Example 14, the method of Example 6 wherein the anchoring element includes first and second tissue anchors and a flexible connecting element therebetween, and wherein the anchoring strap includes opposite first and second ends and the connecting element is coupled to and extends along the anchoring strap between the first and second ends, and wherein the first tissue anchor is positioned in proximity to the first end and the second tissue anchor is positioned in proximity to the second end.

In Example 15, the method of Example 14 wherein the anchoring strap and the anchoring element are pre-assembled and releasably coupled to a delivery tool prior to deployment, the delivery tool including a needle cannula and an open distal end, wherein prior to deployment the first and second tissue anchors are positioned serially within the needle cannula and the anchoring strap and at least a portion of the connecting element is positioned external to the needle cannula.

In Example 16, the method of either of Examples 14 or 15 wherein positioning the anchoring strap against the implantable medical device includes positioning the first end of the anchoring strap against the anatomical feature at a first location and positioning the second end of the anchoring strap against the anatomical feature at a second location, the implantable medical device being positioned between the first and second locations such that the anchoring strap spans across and over the implantable medical device.

In Example 17, the method of either of Examples 15 or 16 wherein positioning the anchoring strap against the implantable medical device and securing the anchoring strap to the anatomical feature includes inserting the open distal end of the delivery tool into the anatomical feature at a first location, ejecting the first tissue anchor from the open distal end and into the anatomical feature, withdrawing the open distal end of the delivery tool from the anatomical feature, inserting the open distal end of the delivery tool into the anatomical feature at a second location, the implantable medical device being positioned between the first and second locations such that the anchoring strap spans across and over the implantable medical device, ejecting the second tissue anchor from the open distal end and into the anatomical feature, withdrawing the open distal end of the delivery tool from the anatomical feature, and tightening the connecting element to secure the implantable medical device between the anatomical feature and the anchoring strap.

In Example 18, the present invention is a method of securing an implantable medical device to or adjacent to an anatomical feature in a patient. The method comprises providing a tissue fixation device releasably coupled to a delivery tool, the tissue fixation device including a flexible, adjustable suture assembly, the delivery tool including first and second needle elements each having a tissue-piercing tip. The implantable medical device is positioned in proximity to the anatomical feature. The tissue piercing tips of the first and second needle elements are inserted into the anatomical feature proximate the implantable medical device. A portion of the tissue fixation device is deployed into the anatomical feature, the tissue-piercing tips of the needle elements are withdrawn from the anatomical feature, and the adjustable suture assembly is tightened to secure the implantable medical device to the anatomical feature.

In Example 19, the method of Example 18 wherein the tissue fixation device further includes first and second tissue anchors coupled to the flexible, adjustable suture assembly, and wherein the first and second tissue anchors are coupled to the first and second needle elements, respectively, and wherein deploying the portion of the tissue fixation device into the anatomical feature includes deploying the first and second tissue anchors and a portion of the adjustable suture assembly into the anatomical feature.

In Example 20, the method of either of Examples 18 or 19 wherein the adjustable suture assembly includes a first suture loop coupled to the first tissue anchor and a second suture loop coupled to the second tissue anchor, and wherein tightening the adjustable suture assembly to secure the implantable medical device to the anatomical feature is performed with the implantable medical device positioned within the first and second suture loops, and wherein tightening the adjustable suture assembly further includes tightening the first suture loop and tightening the second suture loop.

In Example 21, the method of either of Examples 18 or 19 wherein inserting the tissue piercing tips includes inserting the tissue piercing tip of the first needle element into the anatomical feature on a first side of the implantable medical device, and inserting the second tissue piercing tip of the second needle element into the anatomical feature on a second side of the implantable medical device such that a portion of the suture assembly spans across the implantable medical device. Additionally, tightening the adjustable suture assembly includes tightening the suture assembly to secure the implantable medical device against the anatomical feature.

In Example 22, the method of any of Examples 18-21 wherein the first and second needle elements are fixed relative to each other, and wherein inserting the first and second tissue piercing tips includes simultaneously inserting the first and second tissue piercing tips into the anatomical feature.

In Example 23, the method of any of Examples 18-21 wherein the first and second needle elements are individually actuatable, and wherein inserting the first and second tissue piercing tips and deploying the first and second tissue anchors includes first inserting the first tissue piercing tip into the anatomical feature at the first location and deploying the first tissue anchor, and subsequently inserting the second tissue piercing tip into the anatomical feature at the second location and deploying the second tissue anchor.

In Example 24, the method of Example 18 wherein the first needle element is a first needle cannula having a first side opening, and wherein the second needle element is a second needle cannula having a second side opening located at a position distal to the first side opening, and wherein the adjustable suture assembly includes a pre-tied loop for forming a locking element disposed about the first and second needle cannulas prior to deployment of the tissue fixation device.

In Example 25, the method of Example 24 wherein the delivery tool further includes an exchange mandrel having a pre-shaped distal end portion slidably disposed in the first needle cannula, and wherein providing the tissue fixation device releasably coupled to the delivery tool includes providing a portion of the adjustable suture assembly disposed along the first needle cannula and coupled to the distal end portion of the exchange mandrel within the first side opening, and wherein deploying the portion of the tissue fixation device into the anatomical feature includes advancing the distal end portion of the exchange mandrel out the first side opening to the second side opening and engaging the second needle cannula with a passing element on a distal end of the portion of the adjustable suture assembly.

In Example 26, the method of Example 25 wherein withdrawing the tissue piercing tips includes passing the distal end of the portion of the adjustable needle assembly through the pre-tied loop thereby forming the locking element.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIGS. 2A and 2B, respectively, are schematic illustrations of the tissue fixation device of FIG. 1A and a delivery tool for delivering the fixation device according to one embodiment of the present invention.

FIGS. 3A and 3B are perspective and end views of an alternative tissue fixation device secured to the implantable device of FIG. 1A according to another embodiment of the present invention.

FIGS. 9A and 9B are perspective views of the tissue fixation device of FIGS. 8A and 8B mounted on an alternative fixation device delivery tool according to another embodiment of the present invention.

Figure 1A:
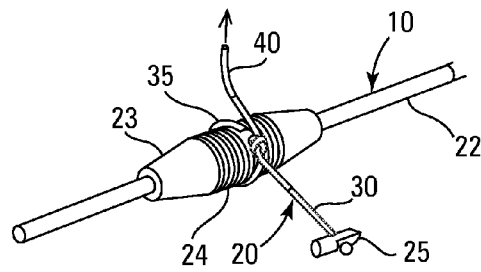
FIG. 1A is a perspective illustration of a tissue fixation device secured to an implantable device according to one embodiment.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1A is a illustration of an implantable medical device, which in the illustrated embodiment is a neurostimulation lead 10 coupled to a tissue fixation device 20 according to one embodiment. As shown in FIG. 1A, the neurostimulation lead 10 has an elongate flexible body 22 and an anchoring sleeve 23 disposed about the body 22. In the illustrated embodiment, the neurostimulation lead 10 can be any conventional or later-developed neurostimulation lead configured for delivering therapeutic stimuli to a patient's central nervous system for pain management and other therapies. As will be appreciated to those skilled in the art, such leads 10 are configured to be coupled at one end to an implantable pulse generator (not shown) configured to generate electric therapy stimuli, and have one or more electrodes at or near the opposite end which when implanted are positioned proximate a specific nerve or nerves selected to provide a desired response to the delivered electrical stimulus. Accordingly, the lead 10 is fixated to tissue near the patient's vertebral column using the fixation device 20 to inhibit or prevent unintended migration of the lead 10 after implantation.

In the illustrated embodiment, the anchoring sleeve 23 is radially compressible and includes a plurality of circumferential grooves 24 longitudinally spaced along the anchoring sleeve 23. As further shown, the fixation device 20 includes a bone anchor 25 and a flexible connecting assembly 30 coupled thereto. In the illustrated embodiment, the connecting assembly 30 is formed from a length of suture material and includes an adjustable loop 35 and a proximal tension line 40 that can be manipulated by the clinician for tightening and cinching up the adjustable loop 35 to secure the lead 10 to the patient anatomy. As shown, the anchoring sleeve 23 is positioned within the adjustable loop 35, with the suture material of the adjustable loop 35 positioned within one of the circumferential grooves 24. In the various embodiments, the anchoring sleeve 23 is slidable along the body 22 of the lead 10 prior to tightening adjustable loop 35. As the adjustable loop 35 is tightened by the clinician, the anchoring sleeve 23 compresses radially to frictionally engage the lead body 22. The anchoring sleeve 23 operates in part to distribute the radial forces imposed by the adjustable loop 35, to avoid undue stress on the lead 10.

Figure 1B:
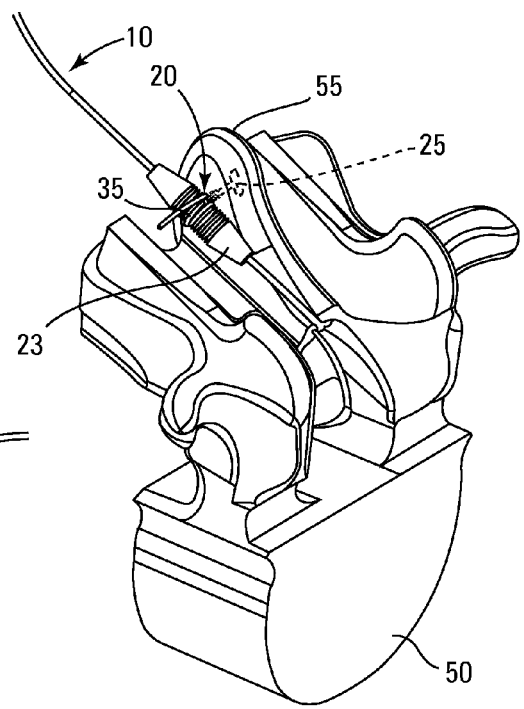
FIGS. 1B and 1C are perspective views of the implantable device of FIG. 1A secured to a vertebral body using the tissue fixation device of FIG. 1A according to one embodiment of the present invention.
Figure 1C:
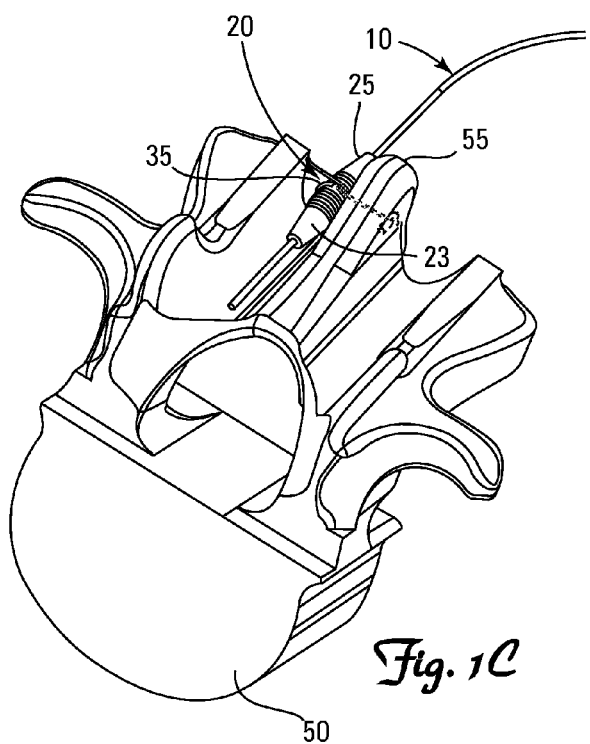

FIGS. 1B and 1C are perspective illustrations showing the lead 10 in an implanted state fixated proximate a patient's vertebra 50 using the fixation device 20 according to one embodiment. As shown in FIGS. 1B and 1C, the lead 10 is secured in place utilizing the spinous process 55 of the vertebra 50 as an anchoring structure. In the illustrated embodiment, the bone anchor 25 is implanted into the spinous process 55 to anchor the fixation device 20 thereto. The anchoring sleeve 23 of the lead 10 extends through the adjustable loop 35 of the fixation device 20, and is thereby secured in place. In the illustrated embodiment, the anchoring sleeve 23 is secured directly against the spinous process 55. In other embodiments, the bone anchor 25 can be embedded into other bony structures or calcified tissue to secure the fixation device 20, and consequently the lead 10, thereto.

FIGS. 2A and 2B are, respectively, schematic views of the fixation device 20 and a fixation device delivery tool 60 for deploying the fixation device 20. As shown in FIG. 2A, the bone anchor has tapered ends 64, 66, an intermediate portion 70 therebetween, and a channel 75 extending through the intermediate portion 70. As further shown, the connecting assembly 30 includes a connecting segment 78 extending through the channel 75 and including a distal locking element 80 and a proximal locking element 82. Additionally, a proximal safety line 84 extends proximally from the locking element 82. In the illustrated embodiment, the locking elements 80, 82 are in the form of knots in the suture material forming the connecting segment 78, the knots positioned on opposite sides of the bone anchor 25 to couple the bone anchor 25 to the connecting assembly 30.

As further shown, in the illustrated embodiment, the adjustable loop 35 is formed by a length of suture material which pierces through the suture material of the connecting segment 78 between the bone anchor 25 and the proximal locking element 82, thereby coupling the adjustable loop 35 to the connecting segment 78 and the safety line 84. As further shown, the adjustable loop 35 includes an adjustable locking element 88, and the proximal tension line 40 extends proximally from the locking element 88. In the illustrated embodiment, the locking element 88 is a knot such as a Roeder or Weston knot that allows for unidirectional sliding movement of the suture material therethrough such that the dimensions of the adjustable loop 35 can be reduced to tighten the loop 35 about the anchoring sleeve 23, but which resists reverse movement and consequent enlargement of the loop 35. In various other embodiments, other locking element structures can be utilized, e.g., pledgets, crimp tubes, and knotless locking elements, to provide the functionality described above.

In the illustrated embodiment, the bone anchor 25 is in the form of a T-anchor and is configured to be insertable into a bore defined in cortical and/or cancellous bone material, wherein the insertion occurs generally in the direction defined between the tapered ends 64, 66. Thereafter, applying tension on the safety line 84 operates to rotate or toggle the bone anchor 25 until firm engagement of the bone material is achieved. In this manner, the bone anchor 25 becomes firmly embedded in the bone, with the connecting segment 78 extending through the bore external to the bone. Thereafter, tension applied to the tension line 40 is resisted by the engagement of the bone anchor 25 and the bone, which operates to tighten the adjustable loop 35 about any structure, e.g., the anchoring sleeve 23 of the lead 10, extending through the loop 35.

As shown in FIG. 2B, the fixation device delivery tool 60, with the fixation device 20 coupled thereto, can be substantially similar or identical to the fixation delivery apparatus 2010 described in co-pending and commonly assigned U.S. patent application Ser. No. 12/552,583 filed Sep. 3, 2009, which is incorporated herein by reference. In the illustrated embodiment, the fixation device delivery tool 60 includes a tubular cannula 100 and a proximal handle 105 coupled thereto. In the illustrated embodiment, the cannula 100 terminates in a relatively blunt distal tip 110. Although not illustrated in FIG. 2B, the fixation device delivery tool 60 further includes an actuating mechanism in the handle 105 coupled to an ejection rod slidably disposed in the tubular cannula 100. Additionally, the fixation device 20 is releasably coupled to the fixation device delivery tool 60 with a portion of the connecting assembly 30, including the proximal tension line 40 and the safety line 84 extending external to the cannula and the bone anchor 25 (not shown in FIG. 2B) disposed within the cannula near the distal tip 110. As further shown, the safety line 84 and the tension line 40 are connected, respectively, to releasable tabs 115 and 118 releasably coupled to the handle 105. The tabs 115, 118 allow for tactile manipulation by the clinician to toggle the bone anchor 25 within the bony structure and to apply tension to the tension line 40 to tighten the adjustable loop 35 as described above.

In use, the bone anchor 25 can be deployed into the spinous process 55 (see FIGS. 1B-1C) according to the techniques described in the aforementioned U.S. patent application Ser. No. 12/552,583. For example, a bone awl or similar tool can be used to form a bore into the surface of the spinous process 55, and the distal tip 110 of the fixation device delivery tool 60 is then inserted into this bore to a desired depth. Next, the bone anchor 25 is ejected from the cannula 105 of the delivery tool 60 and into the bone of the spinous process 55. Once placed into the bone, the clinician can pull on the tab 115 to apply tension to the safety line 84 to toggle the bone anchor 25 until it has firmly engaged the bone. Next, the lead 10 is advance through the adjustable loop 35 of the connecting assembly 30, with the anchoring sleeve 23 positioned within the loop 35. Once the lead 10 is located in the desired position, the clinician pulls on the tension line 40 (by grasping the tab 118) to tighten the loop 35 about the anchoring sleeve 23. Thereafter, any excess lengths of the safety line 84 and the tension line 40 can be cut away using, for example, a scalpel, scissors, a suture cutter, and the like.

Alternatively, the tissue fixation device 20 can be deployed using, for example, the implant delivery tool illustrated in FIGS. 9A-9C of commonly assigned U.S. patent application Ser. No. 12/853,897, the disclosure of which is incorporated herein by reference in its entirety. Use of this implant delivery tool obviates the need to separately form a bore in the spinous process 55 or other bony structure, as the implant delivery tool is configured to penetrate the bone during deployment of the bone anchor 25.

FIGS. 3A and 3B are perspective and end views of an alternative tissue fixation device 200 securing the neurostimulation lead 10 to soft tissue 202 near the patient's spine according to another embodiment of the present invention. As shown in FIGS. 3A and 3B, the tissue fixation device 200 includes an anchoring strap 205 and an anchor band 210. As further shown, the anchor band 210 includes a tissue anchor 215, a connecting element 220 and a locking element 225. The tissue anchor 215 is in the form of a T-anchor configured to be embedded and retained within the soft tissue 202, e.g., muscle, fascial or connective tissue such as the supraspinous ligament. As shown, the connecting element 220 is connected to the tissue anchor 215, and the locking element 225 is connected to the connecting element 220. In various embodiments, the anchor band 210 can be substantially the same or identical to any of the fixation elements (e.g., the fixation elements or anchor bands 308) disclosed in commonly-assigned U.S. patent application Ser. No. 11/120,750, the disclosure of which is incorporated herein by reference in its entirety. As such, the locking element 225 is configured to be slidable along the connecting element 220 in a direction toward the tissue anchor 215, but is configured to resist sliding in a reverse direction so as to retain the tissue anchor 215 and the connecting element 220 under tension when implanted. In various embodiments, the tissue anchor 215 is in the form of a T-anchor or barb, and the locking element 225 is a pledget, knot or similar structure configured to allow increased tension to be applied to the connecting element 220 but to resist reverse movement and subsequent relaxation of this tension. In various embodiments, the anchor band 210 can be deployed using any of the fixation element or anchor band delivery tools (ABDTs) taught in the aforementioned U.S. patent application Ser. No. 11/120,750.

In the illustrated embodiment, in its implanted state, the strap 205 extends circumferentially around the anchoring sleeve 23 of the lead 10 such that the ends of the strap 205 double over each other. As further shown, the connecting segment 220 extends through the doubled-over end portions of the strap 205, with the tissue anchor firmly embedded in the soft tissue 202 and the locking element 225 bearing against the outer surface of the strap 205 so as to maintain the tissue anchor 215 and the connecting element 220 under tension. Accordingly, as shown, the anchor band 210 also operates to secure the strap 205, and consequently the lead 10, to the soft tissue 202.

In use, the strap 205 can be positioned either before or after the lead 10 itself is positioned according to the preference of the implanting clinician. Either way, the anchoring sleeve 23 is positioned over the portion of the strap 205 adjacent to the soft tissue 202, and the strap 205 is then wrapped circumferentially around the anchoring sleeve 23. The anchor band 210 is then deployed to secure the strap 205 and the lead 10 in place. In one embodiment, the anchor band is deployed using a delivery tool (not shown) such as the anchor band delivery tool 400 disclosed in the aforementioned U.S. patent application Ser. No. 11/120,750. In such an embodiment, the sharpened distal tip of the delivery tool is inserted through the doubled over end portions of the strap 205 and into the soft tissue 202 to a desired depth. The tissue anchor 215 is then ejected from the tip of the delivery tool and into or through the soft tissue 202. The delivery tool is then actuated to apply tension to the anchor band 210 and lock the anchor band 210 under tension using the locking element 225, in the manner described in the aforementioned U.S. patent application Ser. No. 11/120,750. Any excess material of the anchor band 210 (e.g., excess suture material) can then be cut away.

In various embodiments, the strap 205 can be formed by any flexible biocompatible material. In various embodiments, the strap 205 is formed of a mesh material. In various embodiments, the strap 205 is also elastic such that it can be stretched as it is wrapped around the anchoring sleeve 23 and thereafter secured under tension to apply a compressive radial force on the anchoring sleeve 23 to enhance fixation of the anchoring sleeve 23 and lead 10 to the soft tissue 202. In various embodiments, the strap 205 includes internal features, e.g., ribs or projections, configured to be complementary to the circumferential grooves on the anchoring sleeves 23. That is, when present, these internal features can engage the features of the circumferential grooves on the anchoring sleeve 23 to inhibit relative axial movement of the anchoring sleeve 23 relative to the strap 205. In various embodiments, the strap 205 can be made of or include materials to encourage or inhibit fibrosus or other tissue in-growth.

Figure 4A:
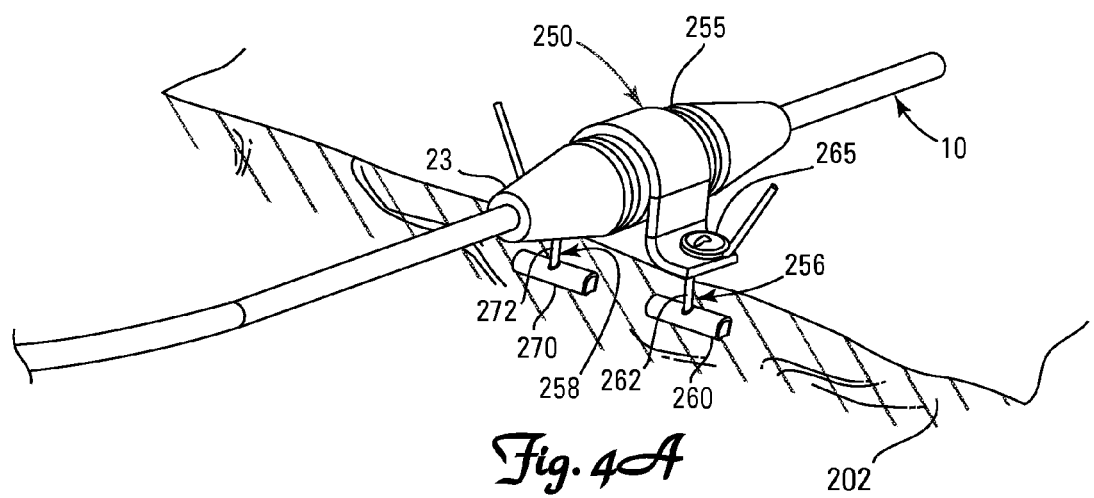
FIGS. 4A and 4B are perspective and end views of an alternative tissue fixation device secured to the implantable device of FIG. 1A according to another embodiment of the present invention.
Figure 4B:
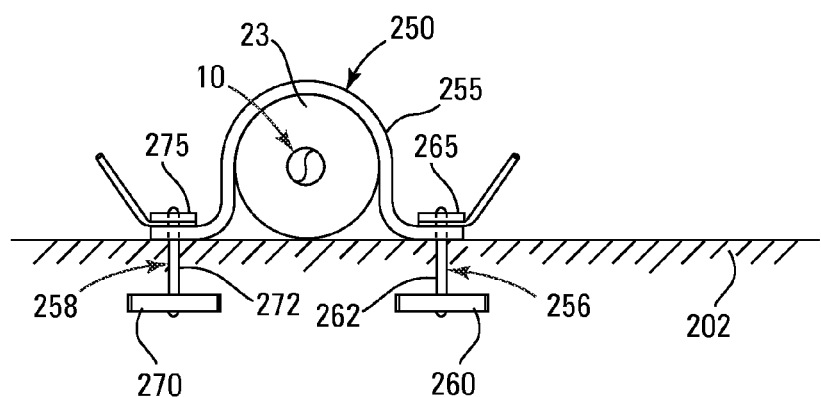

FIGS. 4A and 4B are perspective and end views of an alternative tissue fixation device 250 securing the neurostimulation lead 10 to soft tissue 202 near the patient's spine according to another embodiment of the present invention. As shown in FIGS. 4A and 4B, the tissue fixation device 250 includes an anchoring strap 255 and a pair of anchor bands 256, 258. As further shown, the anchor band 256 includes a tissue anchor 260, a connecting element 262 and a locking element 265. Similarly, the anchor band 258 includes a tissue anchor 270, a connecting element 272 and a locking element 275. The strap 255 and each of the anchor bands 256, 258 can, except as described below, be substantially the same as or identical to the anchoring strap 205 and the anchor band 210 described in connection with the embodiment of FIGS. 3A-3B, except that in the embodiment of FIGS. 4A and 4B the anchoring strap 255 does not wrap substantially completely around the anchoring sleeve 23 and double over on itself. Rather, as shown in FIGS. 4A-4B, the anchoring strap 255 is disposed over the anchoring sleeve 23 of the lead 10 and attached to the soft tissue 202 at opposite ends of the anchoring strap 255 by the respective anchor bands 256, 258. The anchor bands 256, 258 can be deployed and tightened in the same manner described above with respect to the anchor band 215, and consequently, as the fixation elements or anchor bands (e.g., the fixation element/anchor band 308) disclosed in the aforementioned U.S. patent application Ser. No. 11/120,750.

Figure 5A:
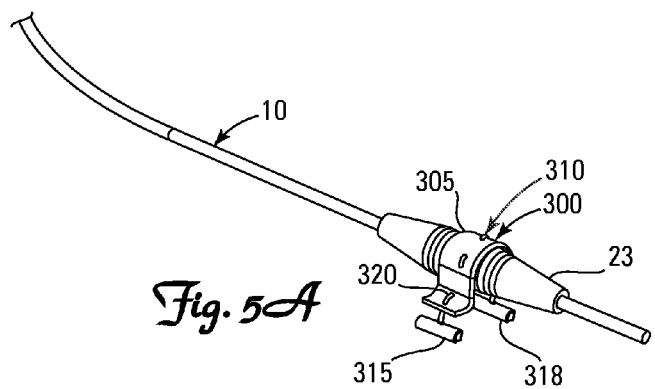
FIGS. 5A, 5B and 5C are perspective views of an alternative tissue fixation device secured to the implantable device of FIG. 1A according to another embodiment of the present invention.
Figure 5B:
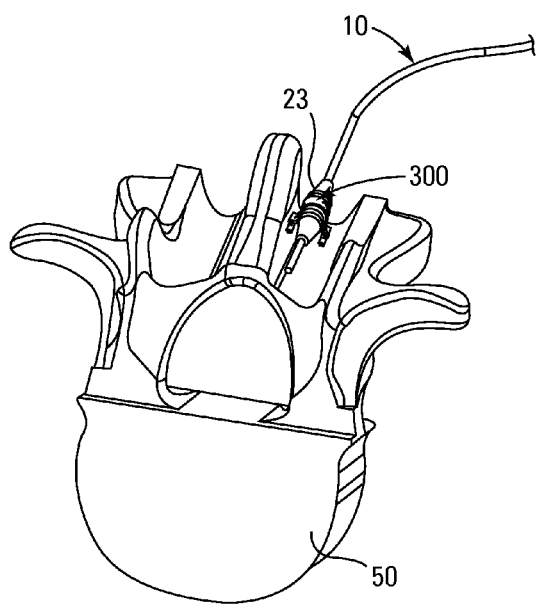
Figure 5C:
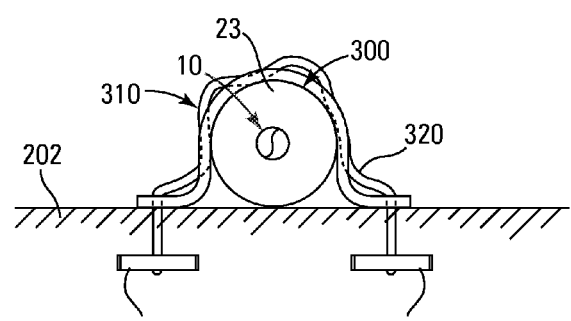

FIGS. 5A-5C are perspective and end views of an alternative tissue fixation device 300 securing the neurostimulation lead 10 to soft tissue 202 near the patient's vertebra 50 according to another embodiment of the present invention. As shown in FIGS. 5A-5C, the tissue fixation device 300 includes an anchoring strap 305 and an adjustable tension band 310 coupled to the anchoring strap 305. As further shown, the adjustable tension band 310 includes a pair of tissue anchors 315, 318 and an adjustable connecting assembly 320 between the tissue anchors 315, 318. As further shown, the adjustable connecting assembly 320 is woven or otherwise extended through and along the anchoring strap 305 to couple these structures together.

In various embodiments, the adjustable tension band 310 and its components are configured to be substantially the same as or identical to any of the fixation devices disclosed in co-pending and commonly assigned U.S. patent application Ser. No. 11/120,750, or the implants illustrated in FIGS. 5A-5C and 6A-6C of co-pending and commonly assigned U.S. patent application Ser. No. 12/853,897. Accordingly, each of the aforementioned patent applications is incorporated herein by reference for all purposes. Thus, in the various embodiments, the adjustable tension band 310 is configured such that the tissue anchors 315, 318 can be deployed into and embedded within the soft tissue 202 and the length of the adjustable connecting assembly 320 can be reduced between the tissue anchors 315, 318, thereby tightening the connecting assembly 320 and securing the anchoring strap 305, and the anchoring sleeve 23 of the lead 10, to the soft tissue 202. In various embodiments, the anchoring strap 305 can be substantially similar or identical to the anchoring straps 205 or 255 discussed above.

Figure 6:
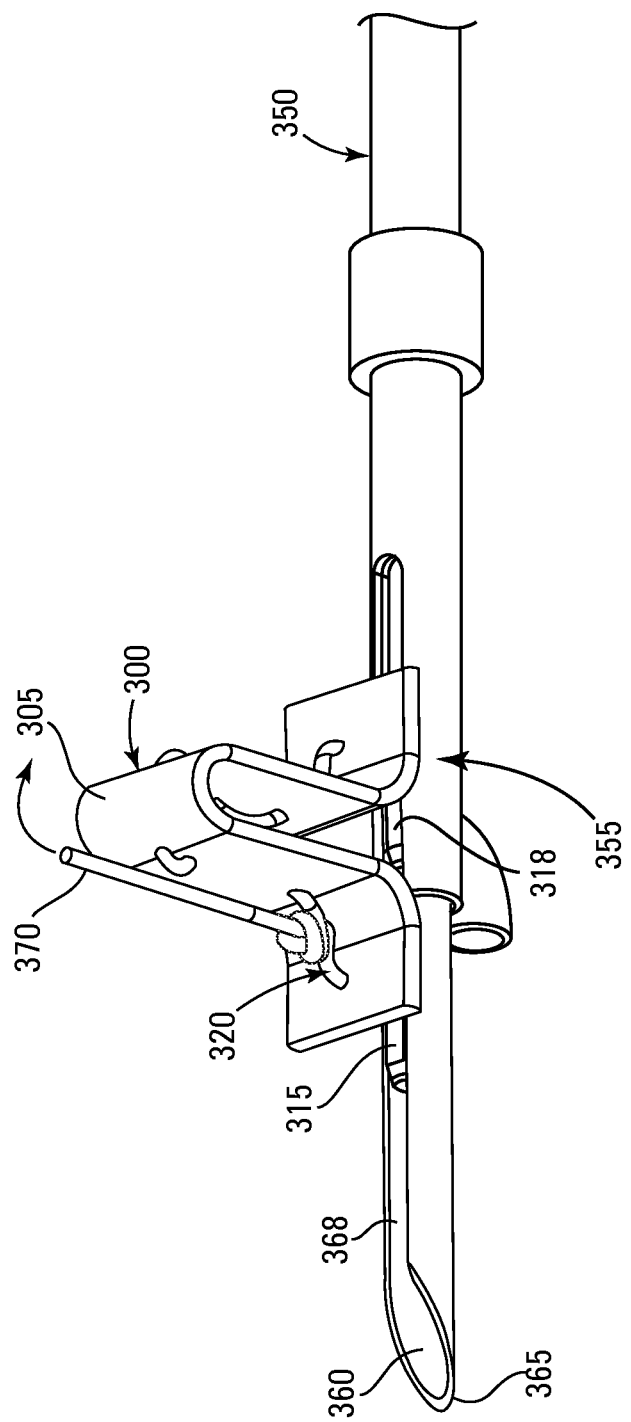
FIG. 6 is a perspective view of a portion of the tissue fixation device secured to a fixation device delivery tool according to another embodiment of the present invention.

FIG. 6 is a perspective view of a portion of the tissue fixation device 300 loaded onto a fixation device delivery tool 350 prior to deployment according to one embodiment of the present invention. As shown in FIG. 6, the fixation device delivery tool 350 includes a tubular needle cannula 355 having an open distal end 360 terminating in a sharp tissue-penetrating tip 365. As further shown, the assembled tissue fixation device 300 is coupled to the needle cannula 355 with the tissue anchors 315, 318 disposed within the needle cannula 355 and the anchoring strap 305 positioned external to the needle cannula 355. Additionally, a portion of the connecting assembly 320 extends through a slot 368 in the needle cannula 355, with a tension line 370 of the connecting assembly 320 extending toward the proximal end of the fixation device delivery tool 350 so that it can be manipulated by a clinician to tighten the connecting assembly 320 as described above.

In various embodiments, the fixation device delivery tool 350 can be substantially similar or identical to, for example, the implant delivery tools illustrated in FIGS. 1 and 7 of the aforementioned U.S. patent application Ser. No. 12/853,897, which is incorporated herein by reference in its entirety, or comparable devices. As such, the fixation device delivery tool 350 includes an actuator mechanism that allows for serial deployment of the tissue anchors 315, 318 into the soft tissue 202, and also for adjusting the adjustable length of the connecting assembly 320 between the tissue anchors 315, 318.

Thus, in use, the lead 10 and the anchoring sleeve 23 (see FIGS. 5A-5C) are positioned as desired, and the tip 365 of the needle cannula 355 is inserted into the soft tissue 202 a desired depth at a location proximate the anchoring sleeve 23. The tissue anchor 315 is then ejected through the open distal end 360 of the needle cannula 355, e.g., by advancing an ejection rod (not shown) disposed within the needle cannula 355 using the above mentioned actuator mechanism. The distal tip 365 is then removed from the soft tissue 202, relocated to a position on the opposite side of the anchoring sleeve 23 with the anchoring strap 305 disposed over the anchoring sleeve 23, and re-inserted into the soft tissue 202. The tissue anchor 318 is then deployed into the soft tissue 202 by advancing the above mentioned ejection rod a second distance. In this regard, the tension band 310 is deployed in substantially the same manner as described in the above mentioned U.S. patent application Ser. No. 12/853,897, except that rather than extending the connecting assembly 320 across a defect in an annulus fibrosus of the disc, the connecting assembly 320 is extended across the anchoring sleeve 23 of the lead 10. Thereafter, the tension line 370 can be pulled so as to tighten the connecting assembly 320 between the tissue anchors 315, 318 and secure the anchoring sleeve 23, and consequently the lead 10, to the soft tissue 202.

Figure 7A:
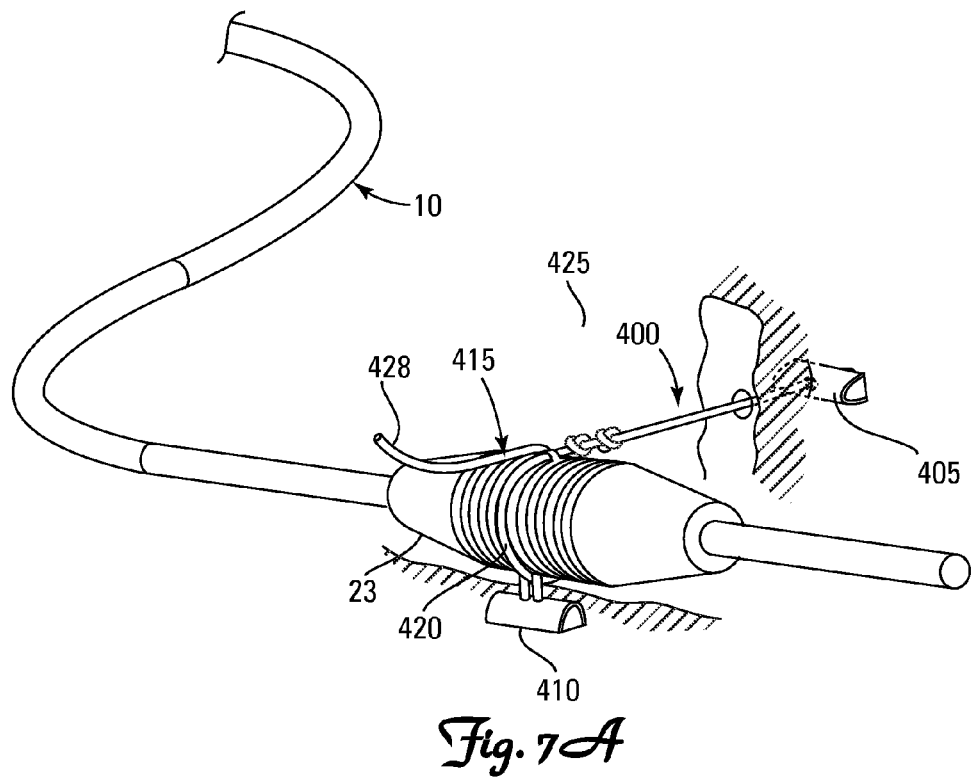
FIG. 7A is a perspective view of an alternative tissue fixation device secured to the implantable device of FIG. 1A according to another embodiment of the present invention.
Figure 7B:
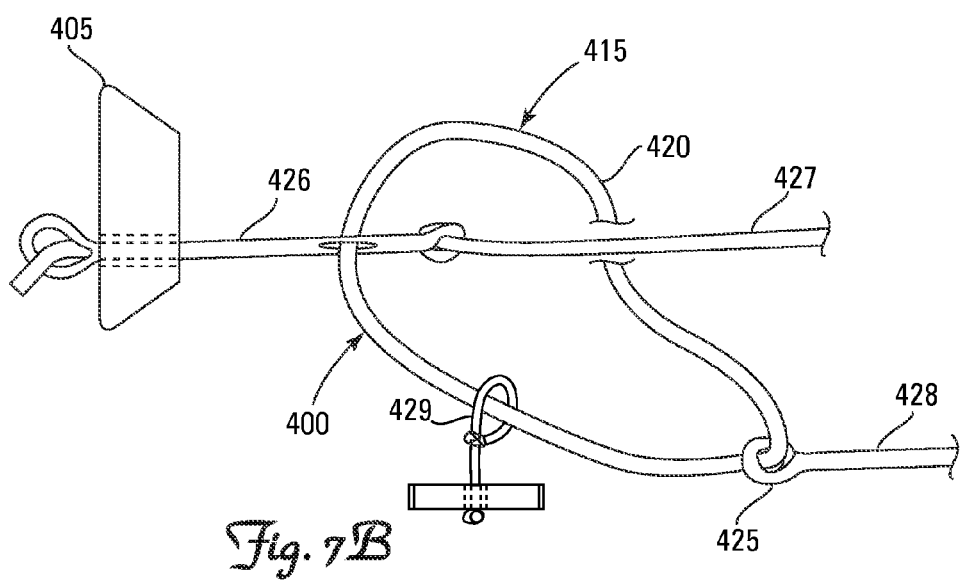
FIG. 7B is a schematic view of the tissue fixation device of FIG. 7A.

FIG. 7A is a perspective view of an alternative tissue fixation device 400 secured to the implantable neurostimulation lead 10 according to another embodiment of the present invention, and FIG. 7B is a schematic view of the tissue fixation device 400 with the lead 10 not shown. As shown in FIGS. 7A-7B, the tissue fixation device 400 includes a bone anchor 405, a tissue anchor 410, and an adjustable connecting assembly 415 connecting the bone anchor 405 and the tissue anchor 410. As further shown, the connecting assembly 415 forms an adjustable loop 420 through which the anchoring sleeve 23 is disposed, and further includes an adjustable locking element 425 to facilitate unidirectional adjustment (i.e., tightening) of the adjustable loop 420. In various embodiments, the locking element 425 can be a knot (e.g., a Roeder knot, a Weston knot, or the like), a mechanical element (e.g., a pledget or comparable structure), or can be in the form of a knotless suture locking arrangement such as the knotless locking elements of the implants illustrated in FIGS. 5A-5C and 6A-6C of co-pending and commonly assigned U.S. patent application Ser. No. 12/853,897, the disclosure of which is incorporated herein by reference.

In various embodiments, the tissue fixation device 400 is in many respects similar or identical to the tissue fixation device 20 described above, with the addition of the tissue anchor 410. Thus, as shown, the bone anchor 405 is fixedly secured to the connecting assembly 415 via a connecting segment 426, and a safety line 427 extends proximally from the connecting segment 426 in the manner described above with respect to the safety line 84 of the tissue fixation device 20. Additionally, a tension line 428 extends from the locking element 425 and is operable to allow the clinician to tighten the adjustable loop 420. In the illustrated embodiment, the tissue anchor 410 is slidably connected to the connecting assembly 415 via a suture loop 429 disposed about the suture material forming the adjustable loop 420. Thus, as the adjustable loop 420 is tightened, the tissue anchor 410 can slide along the loop 420.

In the illustrated embodiment, the tissue fixation device 400 is configured to secure the neurostimulation lead 10 to both bony structures (e.g., the vertebrae) and adjacent soft tissues such as muscle, fascia, or connective tissue. The tissue fixation device 400 may be deployed using, for example, the fixation device delivery tool 350 described above, in which case the bone anchor 405 and the tissue anchor 410 would be positioned serially within the needle cannula 355 prior to deployment. In one embodiment, the bone anchor 405 is positioned distal to the tissue anchor 410 within the needle cannula 355, whereas in other embodiments the tissue anchor 410 would be distal to the bone anchor 405. In another embodiment, the tissue fixation device 400 can be deployed using the implant delivery tool illustrated in FIGS. 9A-9C of commonly assigned U.S. patent application Ser. No. 12/853,897, which is incorporated herein by reference. In such embodiments, the tissue anchor 410 would be positioned proximal to the bone anchor 405 within the delivery tool cannula, which has the capability of forming the bore into the vertebra or other bony structure itself without a separate boring step. Thus, in this embodiment, the bone anchor 405 is deployed first and the tissue anchor 410 second.

In use, either the bone anchor 405 or the tissue anchor 410 is deployed into the respective anatomical feature first, depending on the particular delivery tool utilized. The lead 10 can then be advanced through the loop 420 so that the anchoring sleeve 23 is positioned therein, and the tension line 428 is then pulled to tighten the adjustable loop 420 about the anchoring sleeve 23. Any excess lengths of the connecting assembly 415 are then cut and removed.

Figure 8:
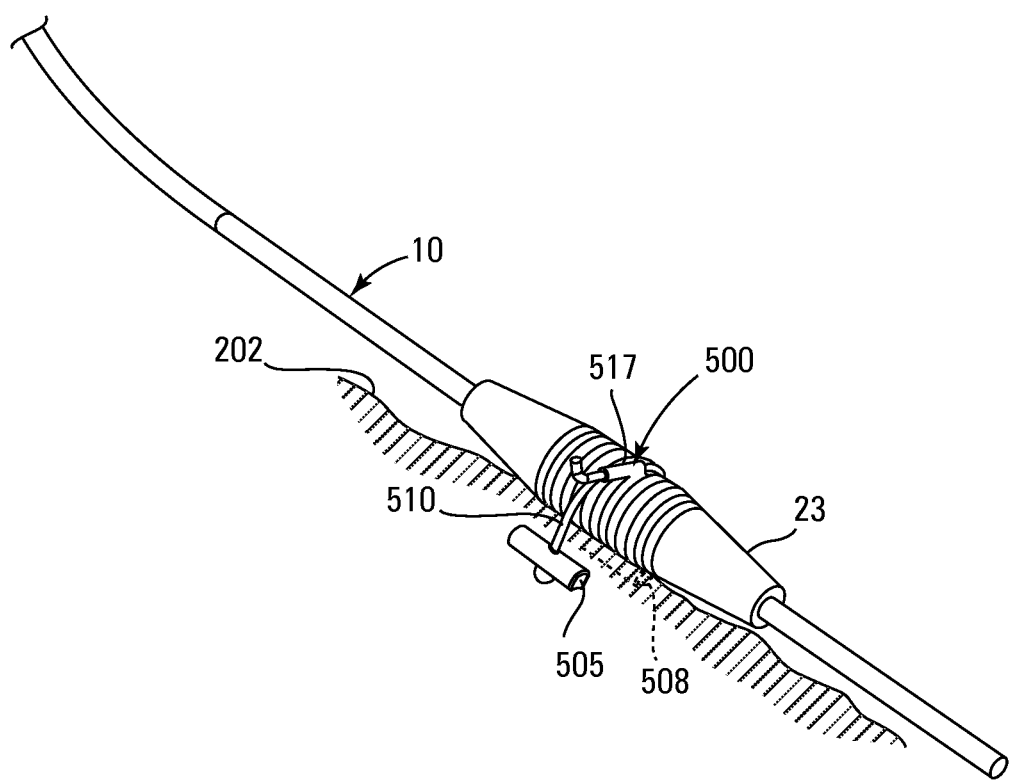
FIG. 8 is a perspective view of an alternative tissue fixation device secured to the implantable device of FIG. 1A according to another embodiment of the present invention.

FIG. 8 is a perspective views of an alternative tissue fixation device 500 secured to the implantable neurostimulation lead 10 according to another embodiment of the present invention. As shown in FIG. 8, the tissue fixation device 500 includes a pair of tissue anchors 505, 508 and a flexible connecting assembly 510 therebetween. As further shown, the tissue anchors 505, 508 are configured to be embedded and anchored within soft tissue 202, e.g., muscle, fascial, or connective tissue, proximate the patient's spine. Additionally, the flexible connecting assembly 510 connects the tissue anchors 505, 508 and includes a locking element 517, which in the illustrated embodiment is a knotless suture locking arrangement in which a length of suture extends within the tubular wall of the suture material forming the connecting assembly 510. Thus, the connecting assembly 510 can be tightened, e.g., by applying tension to a tension line 515 after deploying the tissue anchors 505, 508, to cinch and secure the anchoring sleeve 23 of the lead 10 against the soft tissue 202 in the manner similar to the techniques described above. In various embodiments, the tissue fixation device 500 can be configured to be similar or identical to the implants illustrated in FIGS. 5A-5C and 6A-6C of co-pending and commonly assigned U.S. patent application Ser. No. 12/853,897. Thus, in one embodiment, the tissue anchor 505 can be deployed into the soft tissue 202, the connecting assembly 510 can be extended across the anchoring sleeve 23, and the tissue anchor 508 can then be deployed into the soft tissue 202. Then, the tension line 515 can be pulled to shorten the connecting assembly 510 and secure the anchoring sleeve 23, and consequently the lead 10, against the soft tissue 202. Any excess lengths of the tension line 515 or other aspects of the connecting assembly 510 can then be cut away and removed.

FIGS. 9A and 9B are perspective views of the tissue fixation device 500 mounted on an alternative fixation device delivery tool 550 according to another embodiment of the present invention. As shown in FIGS. 9A and 9B, the fixation device delivery tool 550 includes a handle 555 and a bifurcated needle cannula 557 having a pair of pointed distal end portions 558, 560. As shown, the distal end portions 558, 560 include, respectively, open distal ends 561, 562 and sharpened distal tips 563, 564. Additionally, the fixation device delivery tool 550 further includes a plunger 570 and a releasable tab 575 is coupled the plunger 570 proximal to the handle 555. In the illustrated embodiment, the tissue fixation device 500 is releasably mounted to the distal end portions 558, 560, with the tissue anchors 505, 508 disposed therein. As further shown, the tension line 515 of the connecting assembly 510 extends proximally external to the delivery tool 550 and is connected to the tab 575.

Although not visible in FIGS. 9A and 9B, the plunger 570 is connected to a bifurcated ejection rod having a segment extending within each of the distal end portions 558, 560, and the plunger 570 includes a knob 577 that can be manipulated by the clinician to actuate the plunger 570. Additionally, the plunger 570 is movable longitudinally relative to the handle 555 such that the ejection rod can be extended distally to eject the tissue anchors 505, 508 from the open distal ends 561, 562 of the cannula distal end portions 558, 560. Additionally, as shown, the tab 575 is positioned between the plunger knob 577 and the handle 555 to prevent spontaneous movement of the plunger 570 and ejection of the tissue anchors 505, 508. To operate the plunger 570, the tab 575 is removed such that the plunger 570 can be pushed toward the handle 555.

The distal end portions 558, 560 are selectively spaced to allow the anchoring sleeve 23 (shown in phantom in FIG. 9B) to fit therebetween. Thus, in use, the lead 10 and anchoring sleeve 23 are positioned as desired against the soft tissue to which it will be secured, and the distal end portions 558, 560 are simultaneously inserted into the soft tissue on opposite sides of the anchoring sleeve 23 and the connecting assembly 510 spanning over the anchoring sleeve. The tab 575 is then removed from the plunger 570, which is then pushed distally to deploy the tissue anchors 505, 508 into the soft tissue. The tab 575 is then manipulated by the clinician to pull on the tension line 515, which shortens the connecting assembly 510 between the tissue anchors 505, 508 and tightens or cinches the anchoring sleeve against the soft tissue.

Figure 10A:
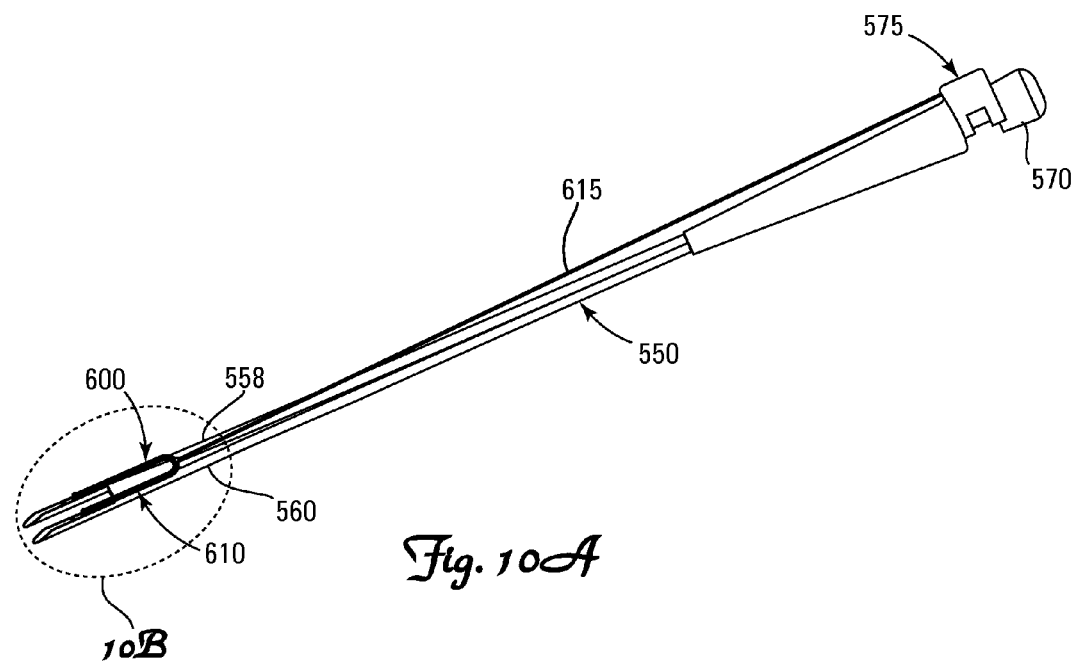
FIGS. 10A and 10B are perspective views of an alternative tissue fixation device mounted on the fixation device delivery tool of FIGS. 9A and 9B according to another embodiment of the present invention.
Figure 10B:
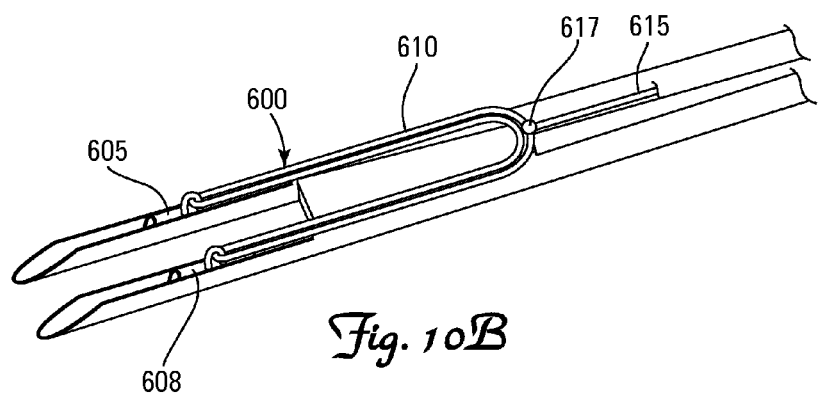

FIGS. 10A and 10B are perspective views of an alternative tissue fixation device 600 mounted on the fixation device delivery tool 550 according to another embodiment of the present invention. As shown in FIGS. 10A and 10B, the tissue fixation device 600 is in many respects similar to or identical to the tissue fixation device 500, and includes a pair of tissue anchors 605, 608 each releasably disposed in the distal end portions 558, 560 of the delivery tool 550, and a flexible connecting assembly 610 connecting the tissue anchors 605, 608. Additionally, the connecting assembly 610 includes a tension line 615 extending and connected to the tab 575 releasably coupled to the plunger 570. The tissue fixation device 600 differs from the tissue fixation device 500 primarily in that the connecting element 610 includes a knot (e.g., a Roeder knot, Weston knot, or the like) as a locking element 617, as compared to the knotless locking element 517 utilized in the tissue fixation device 500. The tissue fixation device 600 is otherwise similar or identical to the tissue fixation device 500, and can be deployed in the same or similar manner to secure the lead 10 to soft tissue.

Figure 11A:
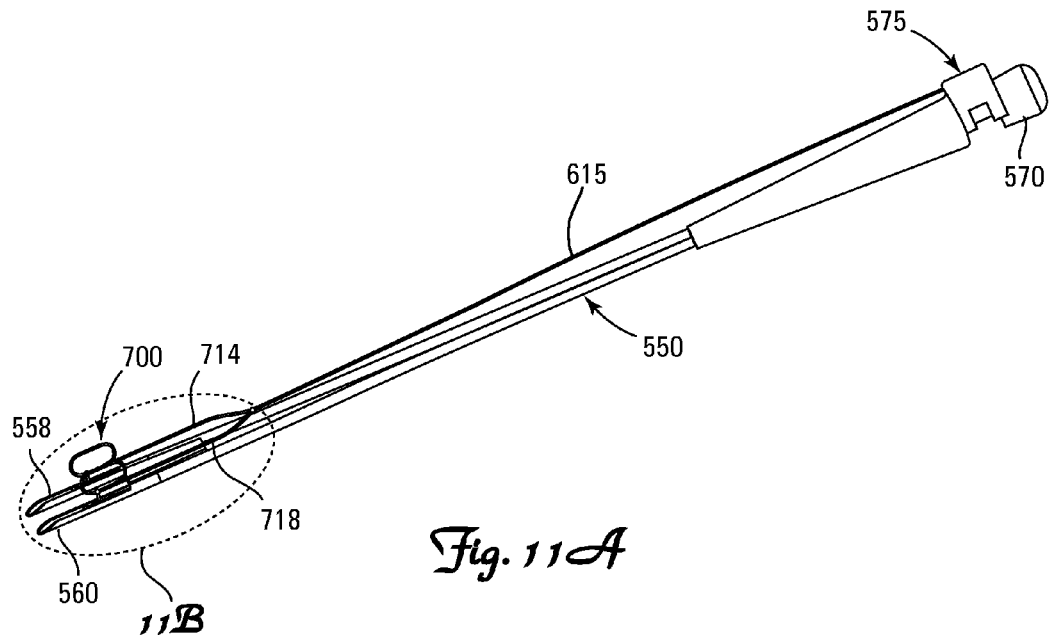
FIGS. 11A and 11B are perspective views of an alternative tissue fixation device mounted on the fixation device delivery tool of FIGS. 9A and 9B according to another embodiment of the present invention.
Figure 11B:
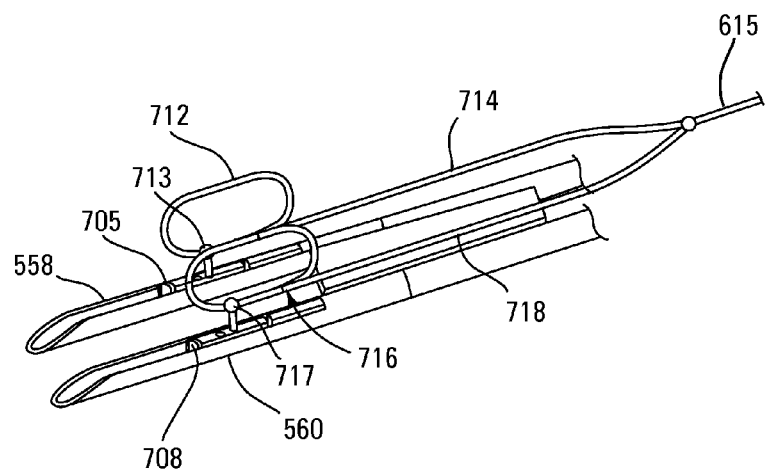

FIGS. 11A and 11B are perspective views of an alternative tissue fixation device 700 mounted on the fixation device delivery tool 550 according to another embodiment of the present invention. As shown in FIGS. 11A and 11B, the tissue fixation device 700 includes a pair of tissue anchors pair of tissue anchors 705, 708 releasably disposed, respectively, in the distal end portions 558, 560 of the delivery tool 550. As further shown, an adjustable suture loop 712 including a locking element 713 and a tension line 714 extending therefrom is connected to the tissue anchor 705, and an adjustable suture loop 716 including a locking element 717 and a tension line 718 extending therefrom is connected to the tissue anchor 708. Additionally, the tension lines 714, 718 are each connected to the releasable tab 575. When used in connection with the tissue fixation device 700 the delivery tool 550 operates in substantially or identically the same manner as described above. In particular, the plunger 570 can be pushed distally to simultaneously eject the tissue anchors 705, 708 into soft tissue to which the lead 10 or other implantable device will be anchored. Additionally, the tab 575 can be manipulated by the clinician to apply tension to the tension lines 714, 718 to reduce the dimensions of the adjustable loops 712, 716. In the illustrated embodiment, the locking elements 713, 717 are in the form of sliding knots, e.g., Roeder, Weston, or the like, which allow unidirectional adjustment of the suture loop dimensions.

In use, the tissue anchors 705, 708 are simultaneously deployed into the soft tissue (e.g, muscle, fascial, or connective tissues) at the desired implantation site, and the lead 10 is positioned with the anchoring sleeve 23 (not shown in FIGS. 11A and 11B) disposed within the interior of the suture loops 712, 716. The tab 575 can then be manipulated to simultaneously apply tension to both tension lines 714, 718 to tighten the adjustable suture loops 712, 716 about the lead anchoring sleeve and secure the lead in place. The tissue fixation device 700 thus advantageously allows the clinician to secure the anchoring sleeve 23, and consequently the lead 10, in place using two separate suture loops at the same time. In other embodiments, however, each tension line 714, 718 can be connected to a separate tabs to allow for separate, selective tightening of each of the suture loops 714, 718.

In various embodiments, alternative tissue fixation devices can be used with and deployed using the tissue fixation device delivery tool 550. In various embodiments, tissue fixation devices utilizing anchoring patches or straps can be utilized. In one embodiment, the tissue fixation device 300 described above can be releasably mounted on and deployed using the delivery tool 550.

In addition, in the illustrated embodiment, the fixation device delivery tool 550 includes fixed distal end portions of the needle cannula 557, thus in effect providing fixed, dual-needles for simultaneously deploying two tissue anchors, in various other embodiments, the fixation device delivery tool 550 can instead include a pair of independent needle cannulas that can be advanced independently of one another. For example, in one embodiment, the fixation device delivery tool 550 can include a pair of needle cannulas with a respective tissue anchor coupled thereto within and near the open distal end, with each needle cannula slidably disposed within an outer tube or sheath and coupled to an actuator mechanism in the handle of the tool 550. In this embodiment, the actuator mechanism can be configured to advance a first one of the needle cannulas independently of the other, to deploy the tissue anchor mounted on or within the advanced needle cannula, to withdraw this needle cannula from the tissue after deployment of the first tissue anchor, and then to advance the other needle cannula into the tissue and subsequently deploy the second tissue anchor.

In one embodiment, in lieu of a pair of needle cannulas, the tissue fixation delivery tool can utilize a pair of solid or substantially solid needles, and the tissue anchors are releasably coupled to the exteriors of the respective needle distal ends by way of hooks or other retaining features formed in or provided on the needles. In one embodiment, the retaining feature(s) can be configured to automatically release or disengage the respective tissue anchor upon retraction of the needle from the tissue.

Figure 12A:
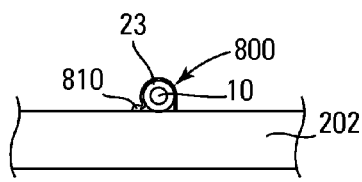
FIGS. 12A-12F are schematic views of a portion of an alternative tissue fixation device and delivery tool for use in fixating the implantable medical device of FIG. 1A according to another embodiment.

FIGS. 12A-12F are schematic views of a portion of an alternative tissue fixation device 800 and tissue fixation device delivery tool 805 according to another embodiment. As shown, the tissue fixation device 800 takes on the form of a suture loop with a pre-tied locking element 810, e.g., a knot such as a Weston knot, enabling the tissue fixation device 800 to secure an implantable medical device such as the neurostimulation lead 10 to soft tissue as illustrated in FIG. 12A. As further shown, the tissue fixation device delivery tool 805 includes dual needle cannulas 812, 814 each capable of penetrating the soft tissue 202 to which the lead 10 is to be secured. As further shown, the needle cannula 812 includes a side opening 818 facing the needle cannula 814, and the needle cannula 814 has a side opening 820 facing the needle cannula 812 and located distal to the side opening 818. Additionally, the tissue fixation device delivery tool 805 includes an exchange mandrel 825 slidable within the needle cannula 812 and including a needle tip element 830, which in its pre-deployed state is pierced through the suture material of the tissue fixation device 800 (see FIG. 12D). As shown, for example, in FIG. 12B, the locking element 810 is initially formed as a suture loop disposed about the needle cannulas 812, 814 prior to deployment. Additionally, the suture material of the tissue fixation device 800 extends along the exterior of the needle cannula 812, and the exchange mandrel 825 extends within the needle cannula 812 with the needle tip element 830 coupled to the suture material proximate and within the side opening 818.

Figure 12B:
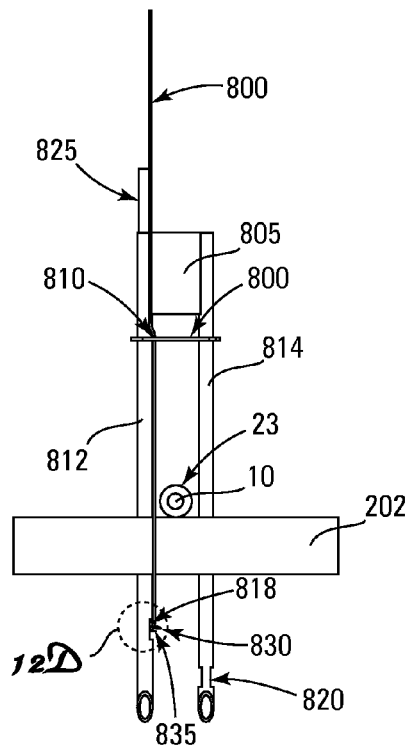
Figure 12C:
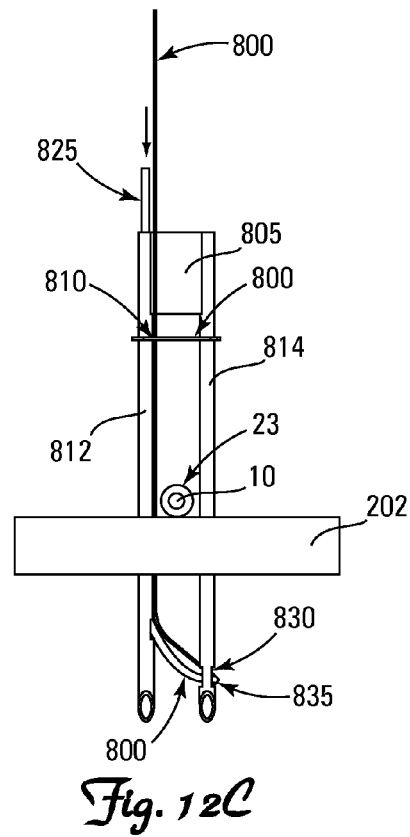
Figure 12D:
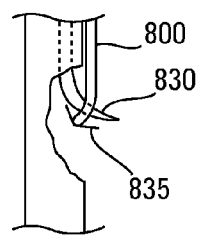
Figure 12E:
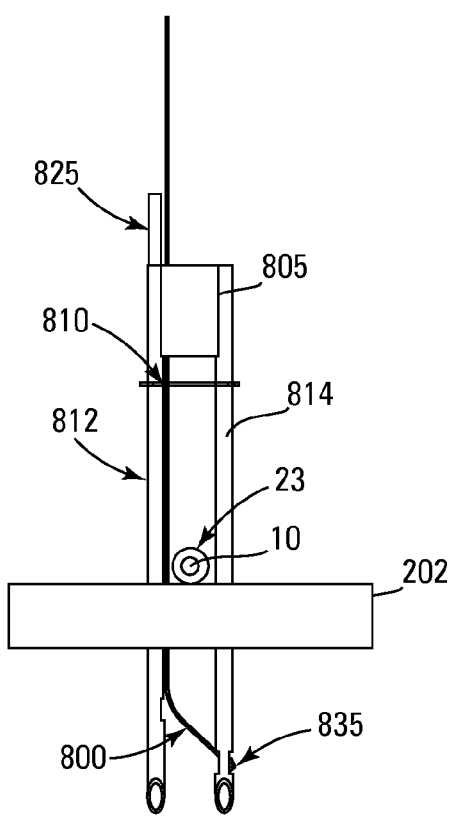
Figure 12F:
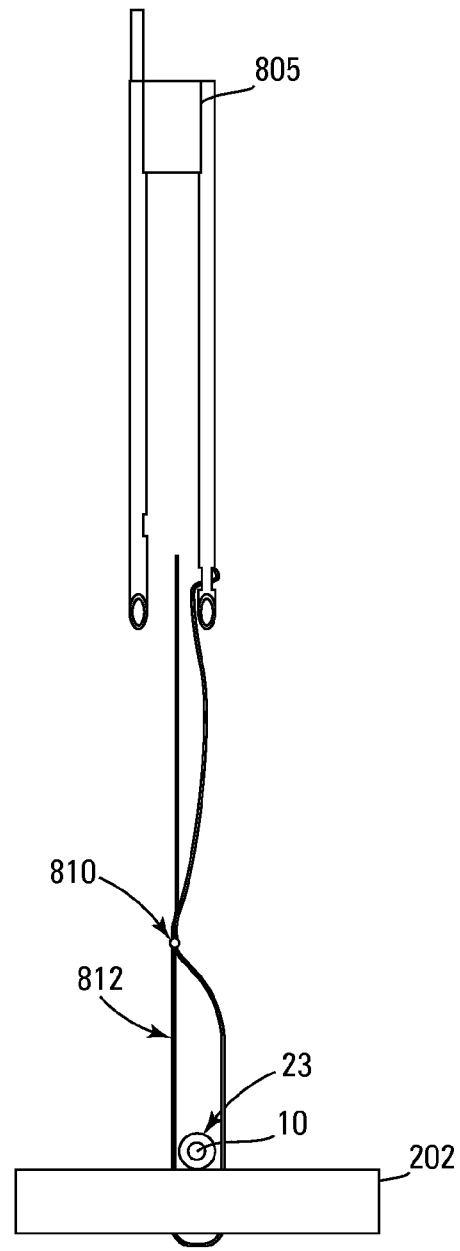

The tissue fixation device delivery tool 805 is configured to form the tissue fixation device 800 in situ by causing the exchange mandrel 825, the needle tip element 830, and the distal end of the suture coupled thereto to pass from the needle cannula 812 through the side opening 820 and into the interior of the needle cannula 814, as shown in FIG. 12C. In the various embodiments, the exchange mandrel 825 has a pre-shaped distal end portion configured to direct the needle tip element 830, and consequently, the distal end of the suture material coupled thereto, out of the side opening 818 and into the side opening 820. Additionally, the distal end of the suture material includes or is formed into a pre-shaped passing element 835 configured to engage the needle cannula 814 within or proximate the side opening 820 (see FIGS. 12C-12D). As shown in FIG. 12E, the exchange mandrel 825 can then be retracted proximally so as to withdraw the needle tip element 830 from the needle cannula 814, whereby the needle tip element 830 is released from engagement with the distal end of the suture material due to the positive engagement of the passing element 835 with the needle cannula 814. The needle cannulas 812, 814 can thereafter be retracted from the tissue 202, whereby the distal end of the suture, including the passing element 835, is routed through the pre-tied locking element 810, which itself slides along and is eventually released from the needle cannulas 812, 814 as shown in FIG. 12F. The resulting structure thus forms the suture loop of the tissue fixation device 800.

Thus, in use, the needle cannulas 812, 814 are inserted into the soft tissue of the implantation site, with the anchoring sleeve 23 of the lead 10 positioned between the needle cannuals 812, 814 and also between the suture of the fixation device 800 and the needle cannula 814 (see FIG. 12B). The exchange mandrel 825 is then advanced distally within the needle cannula 812. In one embodiment, the needle tip element 830 is pierced through the distal end of the suture material of the fixation device 800 during assembly of the fixation device 800 to the delivery tool 805 (see FIG. 12D). In one embodiment, the needle tip element 830 pierces through and engages the suture material as the exchange mandrel is advanced distally within the needle cannula 812.

As shown, the exchange mandrel 825 is further advanced distally so that the needle tip element 830 exits the needle cannula 812 through the side opening 818, with the pre-shaped configuration of the distal end portion of the exchange mandrel 825 directing the needle tip element 830 and the distal end of the suture into the side opening 820 of the needle cannula 814. (FIGS. 12C-12D). As discussed above, the shape of the passing element 835 engages the needle cannula 814 thereby also coupling the suture material thereto so that the needle tip element 830 can be disengaged from the suture and retracted proximally within the needle cannula 812 leaving the suture engaged with the needle cannula 814. (FIG. 12E).

As shown in FIG. 12F, the needle cannulas 812, 814 are then withdrawn from the tissue 202. As further shown, this causes the distal end of the suture to be drawn through the loop forming the pre-tied locking element 810 (e.g., a Weston or similar knot). Additionally, because the suture material is also routed through the tissue 202, the locking element 810 slides over the needle cannulas 812, 814 and is eventually released completely therefrom, as shown in FIG. 12F. The resulting construct forms the suture loop of the fixation device 800 extending within the soft tissue 202 and over the anchoring sleeve 23 and including the adjustable Weston knot as the locking element 810. The tissue fixation device 800 is then tightened to secure the anchoring sleeve 23 to the soft tissue and secure the lead 10 in place. Excess lengths of suture material can then be cut and removed using any suitable means. The tissue fixation device 800 and delivery tool 805 thus provide a quick and efficient means for securing the lead 10 in lieu of manually tying a suture loop.

In various embodiments, the exchange mandrel 825 can be made from a highly flexible and elastic material to allow it to navigate through the needle cannula 812 and into the needle cannula 814. In one embodiment, the exchange mandrel 825 is made of superelastic materials such as nitinol, which also exhibits shape memory so as to retain the pre-formed shape necessary to ensure that it will pass effectively from one needle cannula 812 to the other needle cannula 814. In one embodiment, the exchange mandrel 825 is formed from spring steel or another biocompatible material having comparable strength and flexibility.

In general, the materials used in the various tissue fixation devices and delivery tools described herein can include any number of biocompatible materials having suitable mechanical properties. Materials of which to make the cannulas of the tissue fixation device delivery tools and also the bone and tissue anchors of the tissue fixation devices can include, but are not limited to: metals, such as stainless steel, nickel, titanium alloy, and titanium; plastics, such as polytetrafluoroethylene (PTFE), polypropylene, polyether etherketone (PEEK™), polyethylene, polyethylene teraphthalate (PET) and polyurethane, acrylic, polycarbonate, engineering plastics; and/or composites. The adjustable connecting elements, anchor bands and tension bands of the various tissue fixation devices can likewise be made of any suitable suture material. In various embodiments, these elements are made wholly or partially of size 2-0 or 3-0 force fiber suture material. In short, any suitable materials, whether now known or later developed, can be utilized to construct the various tissue fixation devices and delivery tools described herein, within the scope of the present invention.

Although the various embodiments of the tissue fixation devices and associate delivery tools described herein have been described for use in anchoring implantable neurostimulation leads to bone or tissue, it is emphasized that the devices and methods described herein are readily utilized in securing other implantable devices to the patient anatomy. Exemplary other devices include, for example, other types of implantable stimulation leads or electrodes, catheters, and the like.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method of securing an implantable medical device to or adjacent to an anatomical feature in a patient, the method comprising:
   providing a fixation device coupled to a delivery tool, the delivery tool including a needle cannula having a distal tip, the fixation device including at least one anchor member and a flexible suture assembly including a connecting segment and an adjustable suture loop, wherein the at least one anchor member comprises a first anchor member with a channel, wherein the connecting segment comprises a distal locking element and a proximal locking element disposed on opposite sides of the channel of the first anchor member, wherein each of the distal locking element and the proximal locking element comprises a knot, wherein the adjustable suture loop pierces through the connecting segment between the first anchor member and the proximal locking element;
   inserting the distal tip of the needle cannula into the anatomical feature;
   ejecting the at least one anchor member from the distal tip of the needle cannula into the anatomical feature;
   inserting the implantable medical device within the adjustable suture loop, wherein the implantable medical device is a neurostimulation lead; and
   reducing a dimension of the adjustable suture loop to tighten the adjustable suture loop about the implantable medical device.

2. The method of claim 1, wherein:
   the implantable medical device includes a flexible member and a compressible anchoring sleeve disposed about the flexible member;
   inserting the implantable medical device within the adjustable suture loop includes positioning the anchoring sleeve within the adjustable suture loop; and
   reducing the dimension of the adjustable suture loop to tighten the adjustable suture loop about the implantable medical device includes tightening the adjustable suture loop about the anchoring sleeve.

3. The method of claim 2, wherein the at least one anchor member includes a bone anchor and the anatomical feature includes a bony structure.

4. The method of claim 3, wherein the bony structure is a vertebral body.

5. The method of claim 4, wherein the fixation device further includes a soft tissue anchor slidably coupled to the adjustable suture loop, and wherein the anatomical feature further includes soft tissue proximate the vertebral body, and wherein the method further comprises removing the distal tip of the needle cannula from the vertebral body and subsequently inserting the distal tip of the needle cannula into the soft tissue and ejecting the soft tissue anchor into the soft tissue prior to reducing the dimension of the adjustable suture loop to tighten the adjustable suture loop about the anchoring sleeve.

6. The method of claim 1, further comprising positioning a compressible anchoring sleeve over a portion of the implantable medical device.

7. The method of claim 6, wherein the compressible anchoring sleeve comprises at least one circumferential groove.

8. The method of claim 7, wherein reducing the dimension of the adjustable suture loop comprises tightening the adjustable suture loop about the anchoring sleeve so that a portion of the adjustable suture loop is positioned within at least one of the at least one circumferential groove.

9. The method of claim 6, wherein positioning the compressible anchoring sleeve comprises slidably positioning the compressible anchoring sleeve over the portion of the implantable medical device.

10. The method of claim 1, wherein the flexible suture assembly further includes a proximal tension line configured and arranged for tightening the adjustable suture loop.

11. The method of claim 1, wherein the flexible suture assembly further includes a proximal tension line configured and arranged for tightening the adjustable suture loop and a safety line extending proximally from the proximal locking element.

12. The method of claim 11, wherein providing the fixation device coupled to the delivery tool comprises providing the fixation device with the proximal tension line and safety line extending external to the needle cannula of the delivery tool.

13. The method of claim 12, wherein the delivery tool further includes a handle coupled to the needle cannula and at least one releasable tab coupled to the handle.

14. The method of claim 13, wherein providing the fixation device with the proximal tension line and the safety line extending external to the needle cannula of the delivery tool comprises providing the fixation device with the proximal tension line and safety line extending external to the needle cannula and connected to the at least one releasable tab.

15. The method of claim 14, further comprising using the at least one tab to apply tension to the safety line to rotate or toggle the first anchor member.

16. The method of claim 14, wherein reducing the dimension of the adjustable suture loop comprises using the at least one tab to pull on the proximal tension line to tighten the adjustable suture loop about the implantable medical device.

17. The method of claim 1, wherein the flexible suture assembly further includes a proximal tension line configured and arranged for tightening the adjustable suture loop and a safety line coupled to the adjustable suture loop.

18. The method of claim 17, wherein providing the fixation device coupled to the delivery tool comprises providing the fixation device with the proximal tension line and the safety line extending external to the needle cannula of the delivery tool.

19. The method of claim 18, wherein the delivery tool further includes a handle coupled to the needle cannula and at least one releasable tab coupled to the handle.

20. The method of claim 19, wherein providing the fixation device with the proximal tension line and safety line extending external to the needle cannula of the delivery tool comprises providing the fixation device with the proximal tension line and safety line extending external to the needle cannula and connected to the at least one releasable tab.

21. The method of claim 20, further comprising using the at least one tab to apply tension to the safety line to rotate or toggle the at least one anchor member.

22. The method of claim 20, wherein reducing the dimension of the adjustable suture loop comprises using the at least one tab to pull on the proximal tension line to tighten the adjustable suture loop about the implantable medical device.

* * * * *